(12) United States Patent
Matsutani et al.

(10) Patent No.: US 9,149,275 B2
(45) Date of Patent: Oct. 6, 2015

(54) MEDICAL STAPLER AND MAGAZINE

(75) Inventors: Kanji Matsutani, Utsunomiya (JP); Toshiharu Kamei, Utsunomiya (JP)

(73) Assignee: MANI, Inc., Utsunomiya-shi, Tochigi (JP)

( * ) Notice: Subject to any disclaimer, the term of this patent is extended or adjusted under 35 U.S.C. 154(b) by 588 days.

(21) Appl. No.: 13/579,571

(22) PCT Filed: Feb. 25, 2011

(86) PCT No.: PCT/JP2011/054260
§ 371 (c)(1),
(2), (4) Date: Aug. 17, 2012

(87) PCT Pub. No.: WO2011/105543
PCT Pub. Date: Sep. 1, 2011

(65) Prior Publication Data
US 2012/0325890 A1  Dec. 27, 2012

(30) Foreign Application Priority Data

Feb. 26, 2010  (JP) ................................. 2010-042541

(51) Int. Cl.
*A61B 17/068* (2006.01)

(52) U.S. Cl.
CPC ..... *A61B 17/0684* (2013.01); *A61B 2017/0688* (2013.01)

(58) Field of Classification Search
CPC ................... A61B 17/07207; A61B 17/0684; A61B 17/07271; A61B 17/068; A61B 17/0644; A61B 17/07278
USPC ........................................... 227/175.1, 176.1
See application file for complete search history.

(56) References Cited

FOREIGN PATENT DOCUMENTS

| JP | 2005-533540 A | 11/2005 |
| JP | 2006-305136 A | 11/2006 |
| JP | 2009-131345 A | 6/2009 |

*Primary Examiner* — Michelle Lopez
(74) *Attorney, Agent, or Firm* — Orion Consulting; Joseph P. Farrar, Esq.

(57) ABSTRACT

Width of a space for receiving staples of a magazine is greater than length of the staples and is less than the sum of the length of the staples to ½ of the diameter of the staples, preferably ⅓ thereof or less. The magazine is formed as half split bodies on either side of a rail along the length thereof, a convex positioning part is provided on one of the half split bodies, a concavity for engaging with the positioning convexity is formed on the other half split body, support holes for engaging with positioning parts are formed in the half split bodies, a locking part for holding engagement with the other half split body is provided on said one of the half split bodies, and a to-be-locked part for engaging with the locking part is formed on the other half split body.

1 Claim, 6 Drawing Sheets

Fig. 2
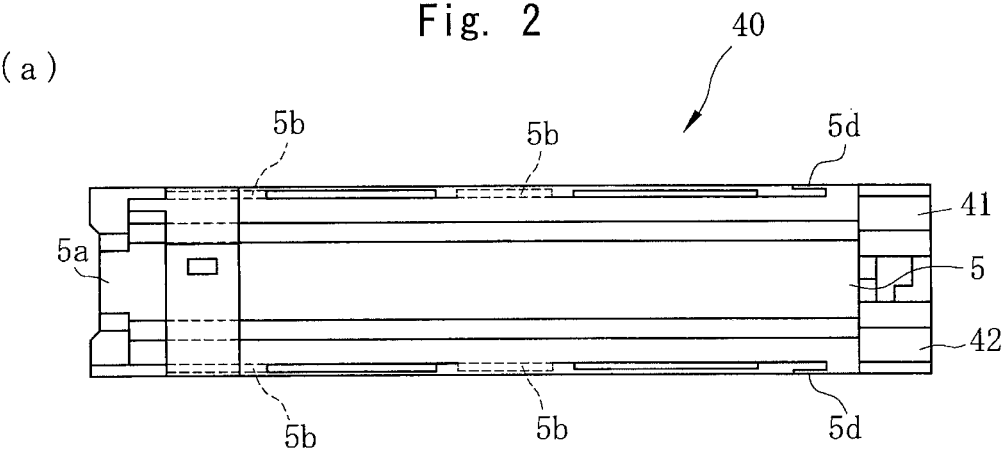
(a)
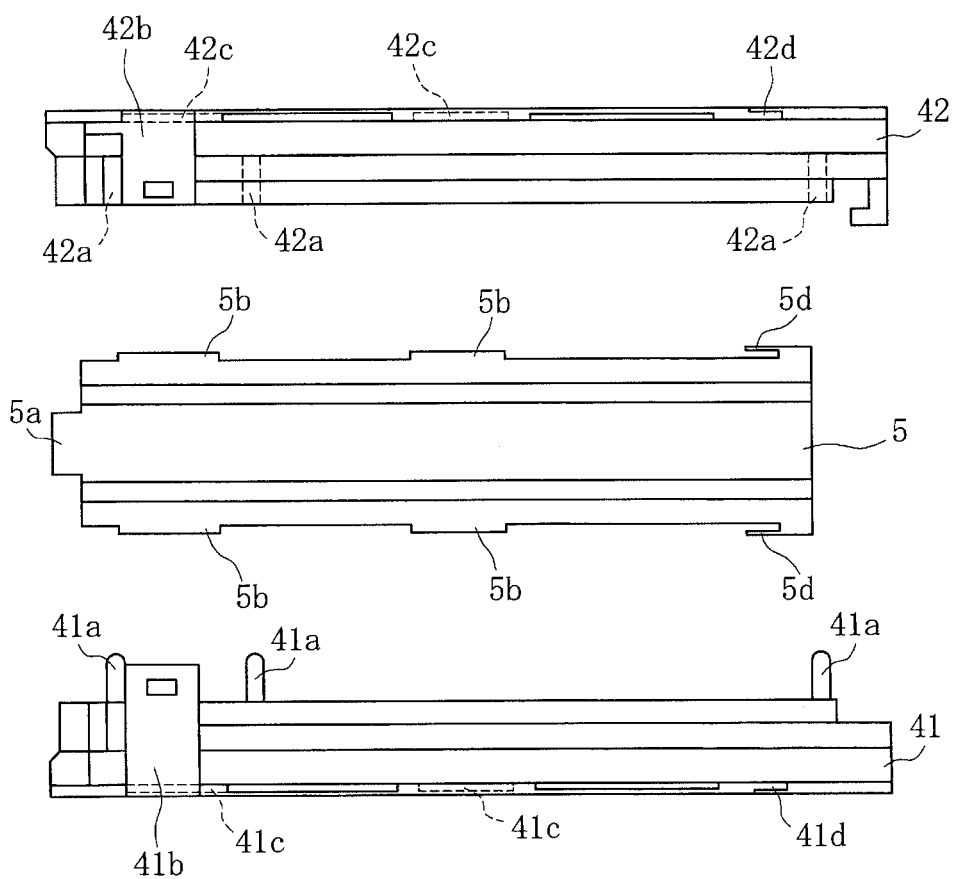
(b)

Fig. 5
(a) 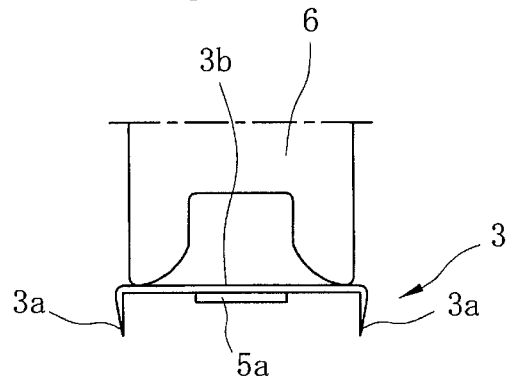
(b) 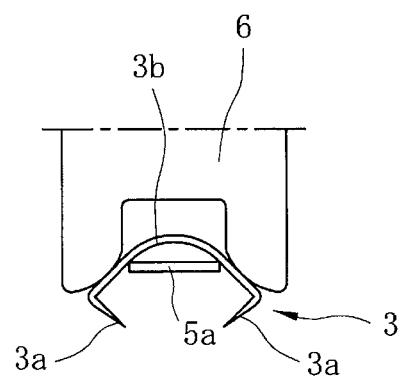
(c) 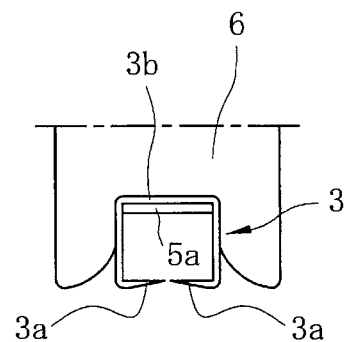

MEDICAL STAPLER AND MAGAZINE

TECHNICAL FIELD

The present invention relates to a medical stapler and a magazine thereof, particularly a medical stapler and a magazine thereof capable of preventing jamming of staples and lowering manufacturing cost.

BACKGROUND ART

A conventional medical stapler as illustrated in FIGS. 4 through 6 disclosed in Patent Document 1 is well known. FIG. 4 shows orthogonal views of a medical stapler, where 4(a) is a top view, 4(b) is a lateral cross-sectional view, and 4(c) is a front view. FIGS. 5(a) to 5(c) are diagrams describing a sequence for forming a staple. FIG. 6 illustrates staples stored in the magazine, where 6(a) is a side view and 6(b) is a cross-sectional view cut along the line I-I of 6(a). A summary thereof will be described below.

A medical stapler 10' illustrated in FIG. 4 is constituted by a housing 1, a lever 2, which is rotatably attached to the housing 1, and a magazine 4, which is attached to the housing 1 in a detachable manner and houses multiple staples 3. The magazine 4 includes a rail 5, which is fixed within the magazine 4, an anvil 5a, which is formed by making an edge of the rail 5 thin and bending it, a ram 6, which is arranged in a movable manner to and back from the edge of the anvil 5a, and a biasing member 7, which biases the ram 6 in a direction away from the edge of the anvil 5a. The rail 5 has a convex structure having a high center and a base part on either side, where a predetermined number of staples 3 are aligned so as to straddle the convexity of the rail 5, and both legs of the staples 3 are placed on the base part on either side of the rail 5. These staples 3 are biased toward the anvil 5a on the edge of the rail 5 by an elastic member 8.

The housing 1 and the lever 2 are made of synthetic resin, such as ABS resin, and formed into shapes in consideration of gripping ease and user-friendliness.

The magazine 4 is formed as a separate body from the housing 1, where the lever 2 and the housing 1 are attached thereto to complete the medical stapler 10'. The magazine 4 is molded integrally using transparent ABS resin, allowing external confirmation of remaining number of the staples stored therewithin.

The staples 3 are stored within a receiving space in the magazine 4 where a predetermined number are lined up, and then placed on the rail 5. The staples 3 are formed by bending a rounded, stainless-steel wire rod into a u-shape, and as shown in FIG. 5(a), are formed having pointed legs 3a so as to reduce resistance when both end portions pierce through a living organism. A portion connecting both of the legs 3a and 3a is referred to as a crown 3b, which is a portion that is bent when suturing the living organism. Moreover, each of the staples 3 is stored with the legs 3a tilting in the advancing direction and the crown 3b tilting in the retreating direction, as shown in FIG. 6(a). The stapler may be downsized by tilting them in this manner at a tilt angle α of 45 to 60 degrees.

Note that length of the crown 3b of the stapler 3 is referred to as staple width, herein.

FIG. 5 are diagrams describing a sequence for forming the staple 3 in order to suture a wound. The stapler 10' is mainly used for suturing a wound on a body surface. When the edge of the stapler 10' is placed on the diseased portion, and the lever 2 shown in FIG. 4(b) is rotated in direction a by application of force, the ram 6 is driven to the lever 2 and lowered, where the edges of the ram 6 finally touch the crown 3b of the staple 3 as shown in FIG. 5(a). When the ram 6 continues to be lowered even further, the crown 3b is bent in a curved shape, as shown in FIG. 5(b). The legs 3a pierce through the skin at this time. When the ram 6 is lowered even further, as shown in FIG. 5(c), the crown 6 is bent at a right angle at both ends of the anvil 5a, the legs 3a become parallel to the anvil 5a in the living tissue beneath the wound, and the staple 3 is bent into a quadrangle, thereby completing a single suture. At this time, only the central portion of the crown 3b appears above the skin, and the other three sides of the quadrangle are buried in the living tissue. Width of the anvil 5a corresponds to the lateral dimension of the quadrangle formed when the staple 3 is formed.

When eliminating the force applied on the lever 2, the lever 2 is rotated in direction b of FIG. 4(b) due to energization force of the bias member 7, the ram 6 is raised, and then returned to the initial position. Repeating the above operation feeds the staples 3 one after another and suturing is repeated.

FIG. 6 illustrates the staples 3 stored in the magazine 4, where 6(a) is a side view and 6(b) is a cross-sectional view cut along the line I-I of 6(a).

A predetermined number of the staples 3 are lined up on the rail 5, pushed by the elastic member 8, and pushed out toward the anvil 5a. Moreover, as described above, the staples 3 in the drawing is slanted at a tilt angle α of 45 to 60 degrees so that the legs 3a tilt in the advancing direction but the crown 3b tilts in the retreating direction. As shown in FIG. 6(b), a staple receiving space 9 of the magazine 4 has width defined by walls 4a and 4b on the left and right sides in the advancing direction, and top and bottom defined by a roof 4c and top surface of the bases of the rail 5. If there is no gap in the vertical direction between the roof and the staples 3 and the width (lateral) direction, the staples 3 cannot progress within the receiving space 9, and the stapler is thus unusable.

Therefore, an appropriate gap is reserved in the width direction and the vertical direction, assuring movement of the staples 3. However, the staples 3 are made by bending round bars, each of the staples 3 are detached, and thereby multiple staples are not lightly connected as are staples for stationary usage. Accordingly, each of the staples 3 is arranged on the bases of the rail 5 and therefore cannot be moved therebelow; however, it is movable above and to the left and right. As a result, there is the following problem in the case where a gap between the left and right walls 4a and 4b is to large. That is, when adjacent staples 3 shift to the left and right, and if the elastic member 8 is then pressed, the staples 3 are pushed and moved toward the left and right walls 4a and 4b orthogonal to the advancing direction, and thrust against the walls 4a and 4b, stuck in without being able to move (which is referred to as "jamming"), and thereby the medical stapler 10 becoming unusable.

Moreover, the staples 3 have a tilt at an angle α within the receiving space 9, as described before; however, when progression is not smooth, the staples 3 rise up and the tilt angle α increases. As a result, the front edges of the sharp legs 3a catch onto the surface of the rail 5, leading to jamming of the staples.

Patent Document 2 proposes relative twisting of a pair of legs of a stapler to provide stable supply of staples. Twisting allows control of the twisted state, allowing smooth supply of staples. However, this configuration does not resolve the problem of jamming of staples due to a gap within the receiving space, and problem of jamming of staples due to catching.

Furthermore, the conventional magazine 4 has an integral structure resulting from injection molding of synthetic resin, formation of space for storing the ram 6 and the biasing member 7 is necessary, and it has a complex form. Therefore, there are problems of a complex metal structure and high manufacturing cost of the magazine.

PRIOR ART DOCUMENTS

Patent Documents

Patent Document 1: JP 2006-305136 A
Patent Document 2: JP 2009-131345 A

DISCLOSURE OF INVENTION

Problem to be Solved by the Invention

The present invention aims to resolve the above problem. A first aim is to provide a medical stapler and a magazine thereof for preventing jamming of staples within the magazine of the medical stapler. Moreover, a second aim is to provide a medical stapler and a magazine thereof allowing reduction in manufacturing cost.

Means of Solving the Problem

In order to attain a first object, a magazine used in a medical stapler according to the present invention is characterized by receiving a plurality of u-shaped medical staples and a rail on which these staples are mounted, wherein width of a space for receiving the staples of the magazine is greater than width of the staples and less than the value resulting from adding the width of the staples to ½ of the diameter of the staples.

A configuration in which hardness of the rail is greater than hardness of the staples, a configuration in which the u-shaped medical staples are received with the legs thereof being tilted in the advancing direction and the body thereof being tilted in the retreating direction, and a configuration in which width of a space for receiving the staples is greater than width of the staples and less than the value resulting from adding the width of the staples to ⅓ of the diameter of the staples are possible.

In order to attain a second object, a magazine used for a medical stapler of the present invention is characterized in that in addition to the above configuration, the magazine further includes half split bodies formed into halves sandwiching either side of a rail along the length of the rail. A configuration in which a convex positioning part is provided on one of the half split bodies formed into halves, a concavity for engaging with the convex positioning part is formed on the other half split body, a positioning part for positioning the rail is formed on the rail, support holes for engaging with the positioning part are formed in the half split bodies, a locking part for holding engagement with the one of the half split bodies is formed on the other half split body, and a to-be-locked part for engaging with the locking part is formed on the one of the half split bodies is possible.

Alternatively, a configuration in which engagement holders for holding engagement of both of the half split bodies on either side with the rail are formed, and engagement receivers for engaging with the engagement holders and holding the engagement with both of the half split bodies.

A medical stapler according to the present invention is characterized in that the half split bodies of any one of the above magazines are attached to a main frame such that force is applied from either side in the direction of mutually adhering the half split bodies.

Result Of The Invention

Width of the receiving space for receiving staples of the magazine is greater than width of the staples, thereby allowing smooth movement of the staples within the magazine. Moreover, if range in which the staple can move within the receiving space along the width thereof is limited and misalignment is within a limited range by making the width of the receiving space be less than the value resulting from adding width of the staple to ½ of the diameter of the staple, the force pushing the staples out surpasses force moving along the width of the receiving space, thereby advancing the staples and preventing jamming of staples.

Furthermore, making the hardness of the rail greater than that of the staples prevents the sharp end of the staples from catching onto the rail even if the tilt of the staples rises up, thereby preventing jamming of staples.

Making the magazine have a half split structure allows a simple metal structure for forming the magazine, and reduction of manufacturing cost of the magazine. A configuration of positioning parts and support holes allows easy positioning of the rail along the width, the length, and the height, as well as easy assembling of the magazine. At the same time, by sandwiching the rail from either side by the half split bodies, the width of the receiving space for the staples formed between the half split bodies may be accurately determined. Moreover, by providing a locking part, which holds engagement with one of the half split bodies, on the other half split body and provision of a to-be-locked part for engaging with the locking part, disassembling of the magazine after it is assembled may be prevented. Furthermore, according to the half split structure of a magazine of the present invention, use of a structure where width of the receiving space is less than the value resulting from adding the width of the staple to ½ of the diameter of the staple allows the same improvement in dimensional accuracy as in the case of integral molded structure, even with the half split structure, and provision of a stapler capable of preventing jamming of staples.

BRIEF DESCRIPTION OF DRAWINGS

FIG. 2 shows bottom views of a magazine, where 2(a) illustrates an assembled state and 2(b) illustrates a disassembled state.

FIGS. 5(a) to 5(c) are diagrams describing a sequence for forming a staple; and

BEST MODE FOR CARRYING OUT THE INVENTION

An embodiment of the present invention is described while referencing the attached drawings.

Figure 1:
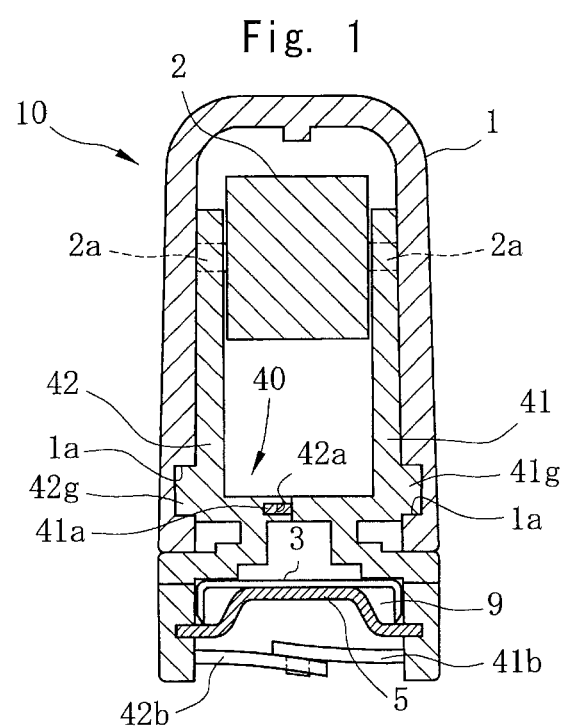
FIG. 1 is a cross-sectional view of substantial parts of a medical stapler according to the present invention.

FIG. 1 is a cross-sectional view of substantial parts of a medical stapler 10 according to the present invention. FIG. 2 shows bottom views of a magazine 40, where 2(a) illustrates an assembled state and 2(b) illustrates a disassembled state. The same reference numerals as in the conventional example indicate the same configuration as the conventional example.

The magazine 40 for the medical stapler 10 of the present invention is divided into two sides sandwiching a rail 5 in the lengthwise direction. One side of the divided magazine 40 is a half split body 41 and the other side is a half split body 42. When it is divided into the half split bodies 41 and 42 in this manner, a method of integrating them by bonding them together with an adhesive may be considered, but that configuration is not employed with the present invention. This is because controlling the amount of adhesive used is difficult in the case of use thereof. That is, if too little adhesive is used, there is a chance of peeling off after attachment. On the other hand, if too much adhesive is used, the adhesive might adhere to the staples 3, and adversely affect the human body. The present invention employs a suture method not having such problems, as described below.

A convex positioning part 41a is formed on the half split body 41, and a concavity 42a that interlocks with the positioning convexity 41a is formed on the other half split body 42. There are multiples (three in FIG. 2) of each of the positioning convexity 41a and the concavity 42a as shown in FIG. 2, allowing positioning of the half split bodies 41 and 42 for uniting them together. A flexible, arm-like locking part 41b is provided near an end of both of the half split bodies 41 and 42 and a flexible, arm-like to-be-locked part 42b is provided near the other end, where the protrusion of the locking part 41b engages with a hole of the to-be-locked part 42b so that the half split bodies 41 and 42 do not easily detach after attachment.

Moreover, as shown in FIG. 2(b), the rail 5 has two pairs of projecting, positioning parts 5b and 5b, and a pair of hook-like engagement holders 5d are formed symmetrically on either side thereof on an end side. The projecting, positioning parts 5b and 5b engage with concave support holes 41c and 42c formed in the half split bodies 41 and 42, respectively, thereby affixing the rail 5 to a predetermined position of the half split bodies 41 and 42. This configuration allows easy positioning of the rail in the width-wise direction, length-wise direction, and height-wise direction, as well as improvement in dimensional accuracy. The hook-like engagement holders 5d engage with engagement receivers 41d and 42d formed on the half split bodies 41 and 42, respectively. Note that while two pairs of the projecting, positioning parts 5b have been provided in this embodiment, one pair may be used. In the case of one pair, the overall balance is improved if it is formed on the front end side (anvil 5a side) of the rail 5.

The magazine is assembled in the following manner. However, the following is merely an example, and the present invention is not limited to this assembly method.

To begin with, the rail 5 is placed between the half split bodies 41 and 42, as shown in FIG. 2(b). The positioning parts 5b and 5b of the rail 5 engage with the concave support holes 41c and 42c formed in either the half split body 41 or 42. At the same time, the hook-like engagement holders 5d are latched to the engagement receiver 41d or 42d of the half split body 41 or 42 to which the positioning parts 5b are engaged. This engages the rail 5 with one of the half split bodies 41 and 42.

Next, the half split body 41 or 42 not engaged is engaged to the rail 5 on the opposite side than said engagement. At this time, the positioning parts 5b and 5b of the rail 5 and the concave support holes 41c and 42c are engaged, the hook-like engagement holders 5d of the rail 5 are engaged with the engagement receiver 41d or 42d formed in the half split body 41 or 42, and the positioning convexity 41a of the half split body 41 is engaged with the concavity 42a of the half split body 42. By engaging the half split bodies 41 and 42 in this manner, once the magazine 40 is assembled, detachment of the half split bodies 41 and 42 may be prevented.

Figure 4:
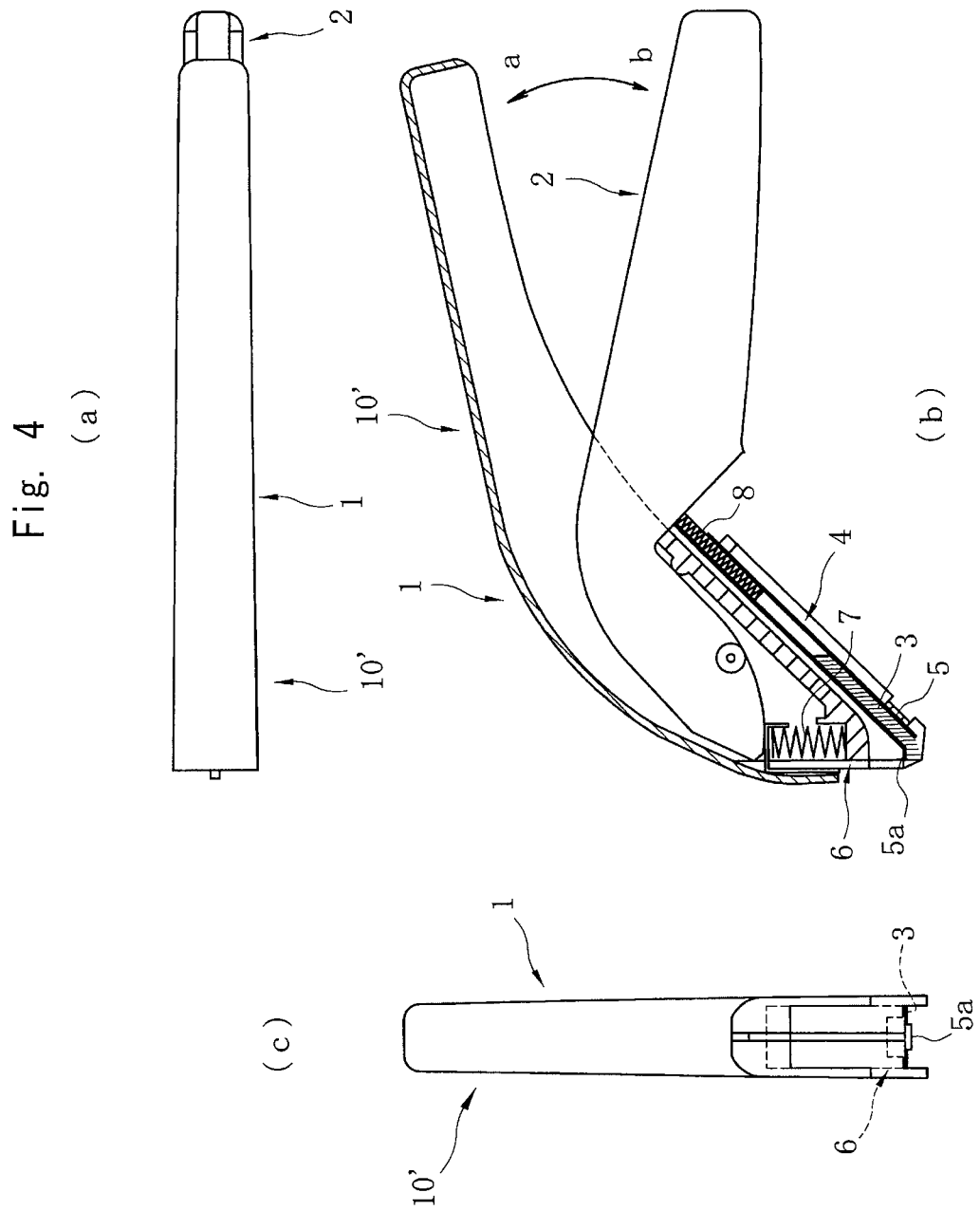
FIG. 4 shows orthogonal views of a conventional medical stapler, where 4(a) is a top view, 4(b) is a lateral cross-sectional view, and 4(c) is a front view.

A receiving space 9 for receiving the staples 3 and a space omitted from the drawing for inserting the ram 6 are formed in the magazine 40 assembled as such, where the receiving space 9 opens at the back end of the magazine 40. A predetermined number of the staples 3 are inserted from this opening, a depressing member is inserted from behind, and the elastic member 8 (see FIG. 4) is then also inserted. Moreover, although not illustrated in the drawing, since the space for receiving the ram 6 opens above the magazine 40, the ram 6 and the biasing member 7 are attached from here, thereby completing the magazine 40.

Once the magazine 40 is assembled, a lever 2 is attached and a housing 1 is also attached. The lever 2 is attached in a turnable manner by engaging an axis 2a to a fitting hole formed in the magazine 40. The housing 1 is attached by convex to-be-attached portions 41g and 42g, which are formed on the magazine 40, engaging with concave attaching parts 1a formed on the housing 1. Through engagement of the attaching parts 1a and the to-be-attached parts 41g and 42g, the half split bodies of the magazine 40 are attached to the housing 1 (main frame) by application of force from either side in the direction of mutually adhering to each other due to resilience of the housing 1, thereby making a secure connection between the magazine 40 and the housing 1. This completes assembling of the medical stapler 10. Usage is the same as described in the conventional example.

Figure 3:
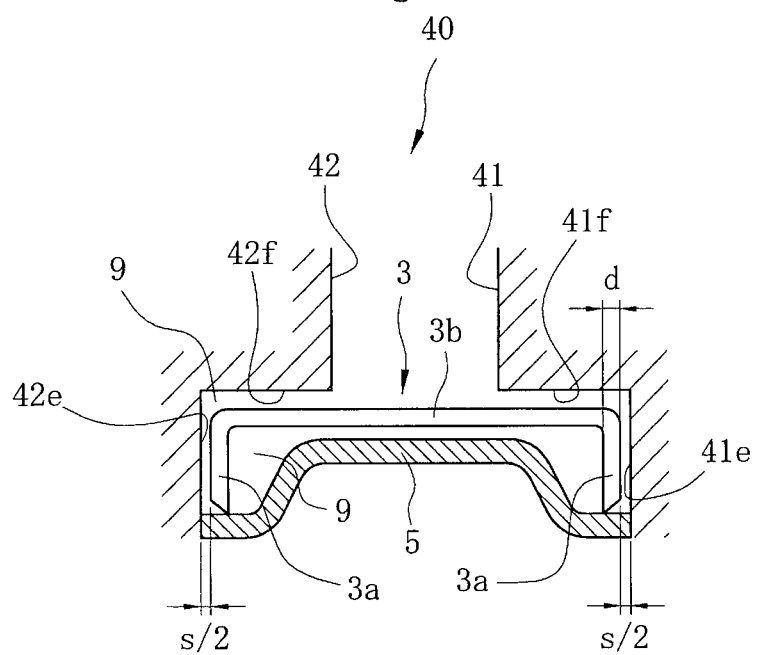
FIG. 3 is a cross-sectional view of substantial parts of the magazine according to the present invention.
Figure 6:
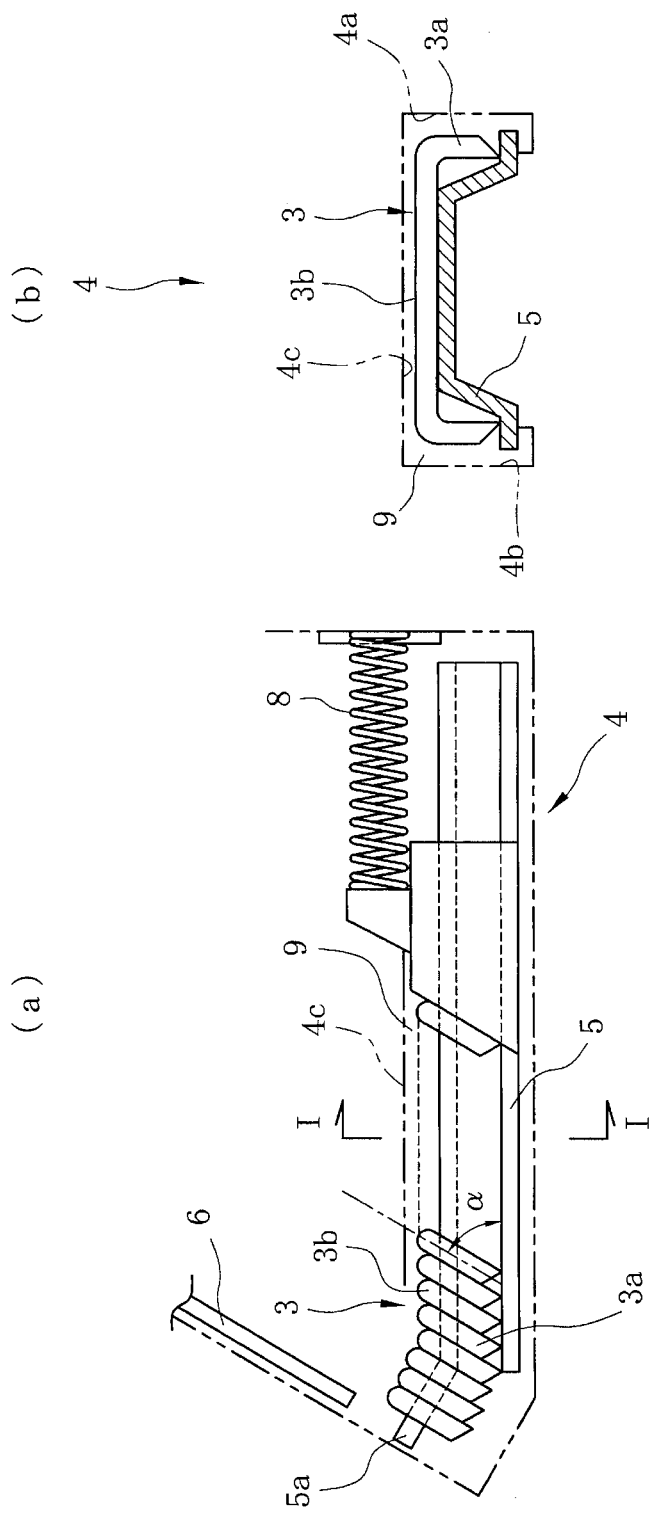
FIG. 6 illustrates staples stored in the magazine, where 6(a) is a side view and 6(b) is a cross-sectional view cut along the line I-I of 6(a).

FIG. 3 is a cross-sectional view of substantial parts of the magazine 40 according to the present invention, illustrating the same place as in FIG. 6(b) described in the conventional example. The same reference numerals as in the conventional example indicate the same configuration thereof.

The staples 3 are stored within the receiving space 9 of the magazine 40; however, the receiving space 9 is defined by the wall 41e of the half split body 41 and the wall 42e of the half split body 42, which are placed running on the right and the left side of the proceeding axis of the staples 3, the base of the rail 5 there underneath, and roofs 41f and 42f of the half split bodies 41 and 42 on the top.

The present invention is characterized in that if s denotes a gap between the left and right walls 41e and 42e of the magazine 40 and the legs 3a of the staples 3, respectively, there is a gap of s/2 on one side, and if d denotes the diameter of the staples 3, a relationship of $0 \leq s \leq d/2$ is established. This configuration is guaranteed through determination of the width of the receiving space 9 by matching the positioning parts 5b and 5b of the rail 5 and the concave support holes 41c and 42c of the half split bodies. If the sum total s of gaps on both sides is less than ½ of the diameter d of the staples 3, and even when the greatest deviance occurs, that is, even when one of adjacent staples 3 adheres to the wall 41e of the receiving space 9 and the other staple 3 adheres to the wall 42e on the other side at the same time, the force by the elastic member 8 pushing in the advancing direction may surpass force pushing the staples 3 against the wall 41e or 42e, thereby advancing the staples 3 without jamming of staples.

Note that even if the gap s is less than d/2, the force pushing the staples 3 against the wall 41e or 42e increases if it exceeds d/3, and therefore value of the gap s is preferably d/3 or less. This is because if it becomes this size, the force pushing the staples against the wall 41e or 42e of the magazine 40 becomes sufficiently small, and there is no more chance of jamming of staples.

Positioning of the rail height-wise is also important in preventing jamming of staples. This configuration is also guaranteed by matching the positioning parts 5b and 5b of the rail 5 and the concave support holes 41c and 42c of the half split bodies, in the same manner as positioning width-wise.

Moreover, the staples may rise up in the direction of increasing the tilt angle since an appropriate gap also exists between the staples 3 and the roofs 41f and 42f. In that case, the legs 3a would conventionally catch onto the rail 5, leading to jamming of staples. On the contrary, according to the present invention, the rail 5 is harder than that of the staples 3. Such configuration may keep the staples from catching onto the rail 5 and prevent jamming of staples. Furthermore, provision of a configuration that makes it difficult for the staples to rise up reliably prevents jamming of staples. Therefore, a configuration where height of the receiving space 9 for the staples 3 is less than the value resulting from adding the height (height up to the top surface of the crown 3b) of the staple 3 to ½ of the diameter of the staple 3 when the staple 3 has a maximum tilt angle of 60 degrees is preferred. According to such a configuration, the force pushing out the staple may surpass force moving along the height of the receiving space, pushing the staple in the advancing direction, and thereby preventing jamming of staples.

In this manner, adoption of a magazine having the half split structure as described above, and use of a configuration where width of the receiving space is less than the value resulting from adding the width of the staple to ½ of the diameter of the staple allow decrease in manufacturing cost, the same improvement in dimensional accuracy as in the case of integral molded structure, even with the half split structure, and provision of a stapler capable of preventing jamming of staples.

DESCRIPTION OF REFERENCE NUMERALS

1: housing
2: lever
3: staple
3a: leg
5: rail
5a: anvil
5b: positioning part
5d: engagement holder
6: ram
9: receiving space
10: medical stapler
40: magazine
41: half split body
41a: convex positioning part
41b: locking part
41c: support hole
41d: engagement receiver
41e: wall
41f: roof
41g: to-be-attached portions
42: half split body
42a: concavity
42b: to-be-locked part
42c: support hole
42d: engagement receiver
42e: wall
42f: roof

The invention claimed is:

1. A magazine for receiving a plurality of u-shaped medical staples and a rail on which these staples are mounted, wherein width of a space for receiving the staples of the magazine is greater than width of the staples and less than the value resulting from adding the width of the staples to ½ of the diameter of the staples,
wherein the magazine is configured by half split bodies formed into halves sandwiching either side of the rail along the length of the rail,
wherein a convex positioning part is provided on one of the half split bodies formed into halves, a concavity for engaging with the convex positioning part is formed on the other half split body, a positioning part for positioning the rail is formed on the rail, support holes for engaging with the positioning part is formed in the half split bodies, a locking part for holding engagement with the one of the half split bodies is formed on the other half split body, and a to-be-locked part for engaging with the locking part is formed on the one of the half split bodies.

* * * * *